United States Patent [19]

Odorisio et al.

[11] Patent Number: 4,831,178
[45] Date of Patent: May 16, 1989

[54] ALIPHATIC ESTERS OF 1,3,2-OXAZAPHOSPHOLIDINES

[75] Inventors: Paul A. Odorisio, Edgewater, N.J.; Stephen D. Pastor, Basel, Switzerland; James L. Hyun, Danbury, Conn.

[73] Assignee: Ciba-Geigy Corporation, Ardsley, N.Y.

[21] Appl. No.: 110,161

[22] Filed: Oct. 19, 1987

[51] Int. Cl.$^4$ ............................................... C07F 9/22
[52] U.S. Cl. ................................... 558/76; 558/81; 524/95
[58] Field of Search ....................... 558/76, 81; 524/95

[56] References Cited

U.S. PATENT DOCUMENTS

| | | | |
|---|---|---|---|
| 2,865,948 | 12/1958 | Fusco | 558/81 |
| 3,172,903 | 3/1965 | Reetz et al. | 558/81 |
| 4,751,319 | 6/1988 | Odorisio et al. | 558/76 |

Primary Examiner—Jacqueline V. Howard
Attorney, Agent, or Firm—Harry Falber

[57] ABSTRACT

1,3,2-oxazaphospholidine aliphatic ester derivatives of the formula

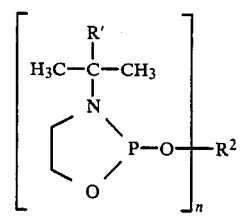

are effective in stabilizing organic materials against oxidative, thermal and actinic degradation, said derivatives being particularly effective as color improvers and process stabilizers in organic materials containing phenolic antioxidants.

24 Claims, No Drawings

ALIPHATIC ESTERS OF 1,3,2-OXAZAPHOSPHOLIDINES

Organic polymeric materials such as plastics and resins are subject to thermal, oxidative and photodegradation. A great variety of stabilizers are known in the art for stabilizing a diversity of substrates. Their effectiveness varies depending upon the causes of degradation and the substrate stabilized. For example, stabilizer effectiveness in reducing volatility may depend upon preventing bond scission in the substrate molecule. Limiting embrittlement and retaining elasticity in a polymer or rubber may require prevention of excessive crosslinking and/or chain scission. Prevention of discoloration may require inhibiting reactions which yield new chromophores or color bodies in the substrate or stabilizer. Problems of process stability and incompatibility must also be considered.

Various oxazaphospholidine compounds have been previously disclosed for a number of different uses. For example, U.S. Pat. No. 2,865,948 discloses aroxy-substituted oxazaphospholidines wherein the end products exhibit pentavalent phosphorus. In addition, certain corresponding trivalent phosphorus compounds are recited as intermediates. These materials are noted for their insecticidal utility. U.S. Pat. No. 3,172,903 discloses 1,3,2-oxazaphospholidines having substitution on the ring nitrogen atom and a variety of aminoethoxy substituents linked to the phosphorus atom. These compounds are noted as fungicides. Broad generic groupings of 1,3,2-oxazaphospholidines with substituents on the ring nitrogen atoms and alkoxy and aroxy substituents on the phosphorus atom are disclosed in U.S. Pat. No. 3,795,612 as antioxidants primarily for lubricants and greases. Organo-phosphorus compounds are noted in U.S. Pat. No. 3,990,994 as components of a polymerization catalyst. U.S. Pat. No. 4,071,583 discloses N-substituted and (P-O)-substituted oxazaphospholidines useful as intermediates in the preparation of polymers. Diaza- rather than oxazaphospholidines are disclosed in DDR No. 146,464 as antioxidants for polyolefins. In addition, application Ser. No. 009,430, filed Feb. 2, 1987, discloses various 1,3,2-oxazaphospholidine derivatives exhibiting aroxy substituents on the phosphorus atom and hindered groups on the ring nitrogen atom.

It has now been determined that the oxazaphospholidines of this invention exhibit a variety of desirable properties which makes them particularly effective and useful as stabilizers. Thus, the compounds protect various substrates such as polyolefins and elastomers against the adverse effects of oxidative and thermal degradation. They are most effective as color improvers and process stabilizers in polyolefin compositions which may contain metal salts of fatty acids and which also contain a phenolic antioxidant. Thus, they serve to substantially reduce color formation resulting from the presence of the phenolic antioxidant and/or from the processing conditions as well as to directly protect the polymer from said processing conditions. They also prevent the discoloration of polyolefin compositions containing hindered amine lght stabilizers or combinations of phenolic antioxidants and organic phosphites.

In summary, the compounds of this invention are unique and exhibit surprising properties distinct from the prior art compounds. The advantages that the instant 1,3,2-oxazaphospholidines exhibit over the prior art are particularly to be noted in their superior polymer stabilizing properties during processing and their low color development when used in combination with conventional phenolic stabilizers.

Accordingly, it is the primary object of this invention to provide a class of aliphatic esters of 1,3,2-oxazaphospholidines which exhibits a broad range of improved stabilization performance characteristics.

It is a further object of this invention to provide compositions of organic materials stabilized against oxidative, thermal and actinic degradation by the presence therein of said derivatives.

It is still a further object to provide such compositions which also contain phenolic antioxidants wherein said derivatives substantially reduce color formation resulting from the presence of said phenols.

Various other objects and advantages of this invention will become evident from the following description thereof.

The compounds of this invention correspond to the formula

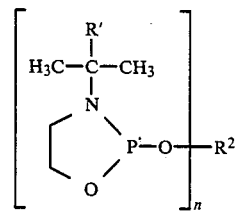

wherein
n is 1-4;

R' is alkyl of 1 to 5 carbon atoms, cycloalkyl of 5 to 6 carbon atoms, phenyl, phenyl substituted by alkyl of 1 to 18 carbon atoms, aralkyl of 7 to 9 carbon atoms or said aralkyl substituted by alkyl of 1 to 18 carbon atoms;

$R^2$, when n is 1, is alkyl of 1 to 18 carbon atoms, cycloalkyl of 5 to 12 carbon atoms, bicycloalkyl of 7 to 18 carbon atoms or tricyclic alkyl of 10 to 20 carbon atoms; and $R^2$, when n is 2-4, is an n-valent aliphatic hydrocarbon of 1 to 18 carbon atoms.

Alkyl in the various R grops is, for example, straight-chain or branched alkyl such as methyl, ethyl, n-propyl, isopropyl, n-butyl, tert-butyl, n-pentyl, n-hexyl, 2-ethylhexyl, n-octyl, decyl, dodecyl and octadecyl; cycloalkyl is, for example, cyclopentyl or cyclohexyl; bicycloalkyl, is for example, bicyclo[2.2.1]heptyl; and tricyclic alkyl is, for example, tricyclo[3.3.1]decyl.

$R^2$ as a bivalent hydrocarbon can be e.g. straight-chain or branched $C_2$-$C_{10}$ alkylene or $C_2$-$C_{12}$-alkylidene such as, for example, ethylene, ethylidene, trimethylene, tetramethylene, pentamethylene, 2,2-dimethylpropane-1,3-diyl, hexamethylene, heptamethylene, octamethylene, decamethylene, 2,2-pentamethylene-propane-1,3-diyl and cyclohexylene.

$R^2$ as a trivalent or tetravalent hydrocarbon can be a group of the following formulae

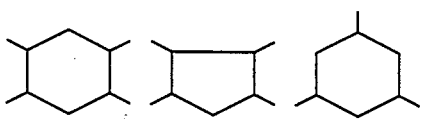

alkanetriyl of 3 to 6 carbon atoms, such as glyceryl or trimethylyl propane; or alkanetetrayl of 4 to 6 carbon atoms such as pentaerythrityl.

Various preferred combinations of substituents and substituent patterns include n=1, R' as methyl and $R^2$ as $C_4$-$C_{12}$ alkyl; n=1, R' as methyl and $R^2$ as cycloalkyl; and n=2, R' as methyl and $R^2$ as $C_4$-$C_{12}$ alkylidene.

The derivatives of this invention are prepared by reacting the appropriately substituted alkanol with the appropriately substituted 2-chloro-1,3,2-oxazaphospholidine in an appropriate solvent system to yield the desired product. The solvent system is preferably a heterocyclic ether such as tetrahydrofuran or an aromatic hydrocarbon such as benzene, toluene or xylene. The reaction temperature ranges from $-30°$ to $150°$ C. The preferred method involves conducting the reaction in the presence of a proton acceptor including metal hydrides such as sodium hydride, lithium hydride, calcium hydride or potassium hydride; alkali and alkaline-eath metal hydroxides such as sodium hydroxide or potassium hydroxide; or metal alkoxides such as sodium methoxide, sodium ethoxide or potassium tert-butoxide.

An alternate approach which allows for the in-situ preparation of the 1,3,2-oxazaphospholidine involves reacting approximately stoichiometric amounts of phosphorus trichloride and the appropriately 2-substituted aminoethanol in a solvent system. The solvent is preferably an ether such as diethylether, tetrahydrofuran or 1,2-dimethoxyethane, or an aromatic hydrocarbon such as benzene, toluene or xylene. The reaction temperature ranges from $-30°$ to $150°$ C. and the reaction can be conducted in the presence of a proton acceptor such as a tertiary amine, for example, triethylamine or pyridine. Thereafter, the appropriately substituted alkanolis added in a comparable solvent and the reaction completed generally at room temperature.

The starting materials needed to prepare the derivatives of this invention are items of commerce or can be prepared by known methods.

The compounds of the present invention are particularly effective in stabilizing organic materials subject to oxidative, thermal and actinic degradation, such as plastics, polymers and resins.

Substrates in which these compounds are particularly useful are polyolefins such as polyethylene and polypropylene; polystyrene, including impact polystyrene, ABS resin, SBR, isoprene, as well as natural rubber, and polyesters including polyethylene terephthalate and polybutylene terephthalate, including copolymers.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with isobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride, vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxides as comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane]terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methylcellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/-butadiene copolymers.

In general, the compounds of the present invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants 1.1. Alkylated monophenols, for example,
2,6-di-tert.butyl-4-methylphenol
2-tert.butyl-4,6-dimethylphenol
2,6-di-tert.butyl-4-ethylphenol
2,6-di-tert.butyl-4-n-butylphenol
2,6-di-tert.butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert.butyl-4-methoxymethylphenol 1.2. Alkylated hydroquinones, for example,
2,6-di-tert.butyl-4-methoxyphenol
2,5-di-tert.butyl-hydroquinone
2,5-di-tert.amyl-hydroquinone
2,6-diphenyl-4-octadecyloxyphenol 1.3. Hydroxylated thiodiphenyl ethers, for example
2,2'-thio-bis-(6-tert.butyl-4-methylphenol)
2,2'-thio-bis-(4-octylphenol)
4,4'-thio-bis-(6-tert.butyl-3-methylphenol)
4,4'-thio-bis-(6-tert.butyl-2-methylphenol)

1.4. Alkylidene-bisphenols, for example,
2,2'-methylene-bis-(6-tert.butyl-4-methylphenol)
2,2'-methylene-bis-(6-tert.butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert.butylphenol)
2,2'-ethylidene-bis-(4,6-di-tert.butylphenol)
2,2'-ethylidene-bis-(6-tert.butyl-4-isobutylphenol)
4,4'-methylene-bis-(2,6-di-tert.butylphenol)
4,4'-methylene-bis-(6-tert.butyl-2-methylphenol)
1,1-bis-(5-tert.butyl-4-hydroxy-2-methylphenyl-butane
2,6-di-(3-tert.-butyl-5-methyl-2-hydroxybenzyl)-4-methylphenol
1,1,3-tris-(5-tert.-butyl-4-hydroxy-2-methylphenyl)-butane
1,1-bis-(5-tert.butyl-4-hydroxy-2-methylphenyl)-3-n-dodecylmercaptobutane
ethylenglycol-bis-[3,3-bis-(3'-tert.butyl-4'-hydroxyphenyl)-butyrate]
di-(3-tert.butyl-4-hydroxy-5-methylphenyl)-dicyclopentadiene
di-[2-(3'-tert.butyl-2'-hydroxy-5'-methyl-benzyl)-6-tert.butyl-4-methylphenyl]-terephthalate.

1.5. Benzyl compounds, for example,
1,3,5-tri-(3,5-di-tert.butyl-4-hydroxybenzyl)-2,4,6-trimethylbenzene-di-(3,5-di-tert.butyl-4-hydroxybenzyl)-sulfide
3,5-di-tert.butyl-4-hydroxybenzyl-mercapto-acetic acid isooctyl ester
bis-(4-tert.butyl-3-hydroxy-2,6-dimethylbenzyl)dithiolterephthalate 1,3,5-tris-(3,5-di-tert.butyl-4-hydroxybenzyl)-isocyanurate
1,3,5-tris-(4-tert.butyl-3-hydroxy-2,6-dimethylbenzyl)isocyanurate
3,5-di-tert.butyl-4-hydroxybenzyl-phosphoric acid-dioctadecyl ester
3,5-di-tert.butyl-4-hydroxybenzyl-phosphoric acid-monoethyl ester, calcium-salt 1.6. Acylaminophenols, for example,
4-hydroxy-lauric acid anilide
4-hydroxy-stearic acid anilide
2,4-bis-octylmercapto-6-(3,5-tert.butyl-4-hydroxyanilino)-s-triazine
octyl-N-(3,5-di-tert.butyl-4-hydroxyphenol)-carbamate 1.7. Esters of β-(3,5-di-tert-butyl-4-hydroxyphenyl)-propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.8. Esters of β-(5-tert-butyl-4-hydroxy-3-methylphenyl)propionic acid with monohydric or polyhydric alcohols, for example,

| | |
|---|---|
| methanol | diethyleneglycol |
| octadecanol | triethyleneglycol |
| 1,6-hexanediol | pentaerythritol |
| neopentylglycol | tris-hydroxyethyl isocyanurate |
| thiodiethyleneglycol | di-hydroxyethyl oxalic acid diamide |

1.9. Amides of β-(3,5-di-tert-butyl-4-hydroxyphenyl)-propionic acid for example,
N,N'-di-(3,5-di-tert.butyl-4-hydroxyphenylpropionyl)-hexamethylenediamine
N,N'-di-(3,5-di-tert.butyl-4-hydroxyphenylpropionyl)-trimethylenediamine
N,N'-di-(3,5-di-tert.butyl-4-hydroxyphenylpropionyl)-hydrazine 2. UV Absorbers and Light Stabilizers 2.1. 2-(2'-Hydroxyphenyl)-benzotriazoles, for example, the 5'-methyl-, 3',5'-di-tert.butyl-, 5'-tert.butyl-, 5'-(1,1,3,3-tetramethylbutyl)-, 5-chloro-3',5'-di-tert.butyl-, 5-chloro-3'-tert.butyl-5'-methyl-, 3'-sec.butyl-5'-tert.butyl-, 4'-octoxy, 3',5'-di-tert.amyl-, 3',5'-bis(α,α-dimethylbenzyl)-derivative.

2.2. 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivative.

2.3. Esters of optionally substituted benzoic acids for example, phenyl salicylate, 4-tert.butyl-phenylsalicylate, octylphenyl salicylate, dibenzoylresorcinol, bis-(4-tert.butylbenzoyl)-resorcinol, benzoylresorcinol, 3,5-di-tert.butyl-4-hydroxybenzoic acid 2,4-di-tert.butyl-phenyl ester and 3,5-di-tert.-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-di-ethanolamine, nickel dibutyldithiocarbamate, nickel sats of 4-hydroxy-3,5-di-tert.butylbenzylphosphonic acid monoalkyl esters, such as of methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazol, optionally with additional ligands.

2.6. Sterically hindered amines, for example bis-(2,2,6,6-tetramethylpiperidyl)-sebacate, bis-(1,2,2,6,6-pentamethylpiperidyl)-sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert.octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5-tetramethyl-piperazinone).

2.7. Oxalic acid diamides, for example, 4,4'-dioctyloxyoxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis(3-dimethylaminopropyl)oxalamide, 2-ethoxy-5-tert.butyl-2'-ethyloxanilide and its mixture with 2-ethoxy-2'-ethyl-5,4'-di-tert.butyloxanilide and mixtures of ortho- and para-methoxy- as well as of o- and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-traizole, bis-benzylidene-oxalic acid dihydrazide.

4. Phosphites and phosphonites, for example, triphenyl phosphite, diphenylalkyl phosphites, phenyldialkyl phosphites, tri-(nonylphenyl)phosphite, trilauryl phosphite, trioctadecyl phosphite, di-stearyl-pentaerythritol diphosphite, tris-(2,4-di-tert.butylphenyl)-phosphite, di-isodecylpentaerythritol diphosphite, di-(2,4-di-tert.butylphenyl)pentaerythritol diphosphite, tristearylsorbitol triphosphite, tetrakis-(2,4-di-tert.butylphenyl)-4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc-dibutyl-dithiocarbamate, dioctadecyldisulfide, pentaerythritol-tetrakis-(β-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium cabonate, silicates, glass fibers, asbestos, talc, kaolin, mica, barium sulfate, metal oxides and hydroxides, carbon black, graphite.

10. Other additives, for example, plasticizers, lubricants, emulsifiers, pigments, optical brighteners, flameproofing agents, anti-static agents, blowing agents and thiosynergists such as dilaurylthiodipropionate or distearylthiodipropionate.

While the instant oxazaphospholidines can be beneficially used as stabilizers for a variety of substrates, particularly the polyolefins, both alone and in conjunction with other coadditives, the introduction of the instant oxazaphospholidines into polyolefins, optionally containing various alkali metal, alkaline earth metal and aluminum salts of higher fatty acids (see Additive #7 hereinabove), with hindered phenolic antioxodiants results in enhanced and particularly salubrious protection to such substrates in terms of reducing color formation stemming from the presence of the phenols. Such phenolic antioxidants include n-octadecyl 3,5-di-tert-butyl-4-hydroxyhydrocinnamate, neopentanetetrayl tetrakis-(3,5-di-tert-butyl-4-hydroxyl-hydrocinnamate), di-n-octadecyl 3,5-di-tert-butyl-4-hydroxybenzyl-phosphate, 1,3,5-tris(3,5-di-tert-butyl-4-hydroxy-benzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-di-oxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenyl), 1,3,5-tris(2,6-di-methyl-4-tert-butyl-3-hydroxybenzyl)isocyanurate, 1,1,3-tris-(2-methyl-4-hydroxy-5-tert-butylphenyl)butane, 1,3,5-tris-[2-(3,5-di-tert-butyl-4-hydroxyhydrocinnamoyloxy)-ethyl]-isocyanurate, 3,5-di-(3,5-di-tert-butyl-4-hydroxybenzyl)-mesitol, hexamethylene bis(3,5-di-tert-butyl-4-hydroxyhydrocinnamate), 1-(3,5-di-tert-butyl-4-hydroxyanilino-3,5-di(octylthio)-s-triazine, N,N'-hexamethylene-bis(3,5-di-tert-butyl-4-hydroxyhydrocinnamide), calcium bis(ethyl-3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis-[2-(3,5-tert-butyl-4-hydroxyhydroxo-cinnamoyloxy)ethyl]-oxamide, and preferably neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris-(3,5-di-tert-butyl-4-hydroxybenzyl)isocyanurate, 2,6-di-tert-butyl-p-cresol or 2,2'-ethylidene-bis(4,6-di-tert-butylphenol).

Likewise, the instant compounds prevent color formation when hindered amine light stabilizers are present, such hindered amines including bis(1,2,2,6,6-pentamethyl-4-piperidyl)-2-n-butyl-2-(3,5-di-tert-butyl-4-hydroxybenzyl)malonate; bis(2,2,6,6-tetramethyl-4-piperidyl)sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

The following examples illustrate the embodiments of this invention. In these examples, all parts given are by weight unless otherwise specified.

EXAMPLE 1

2-Octoxy-3-tert-butyl-1,3,2-oxazaphospholidine

A solution of 8.7 ml (0.10 mol) of phosphorus trichloride in 190 ml of diethyl ether is cooled at 0° C., in a 1 liter, three neck flask equipped with a mechanical overhead stirrer, a thermometer and an addition funnel, under a nitrogen sweep. A solution of 27.8 ml (0.20 mol) of triethylamine and 11.7 g (0.10 mol) of 2-tert-butyl-aminoethanol in 50 ml of diethyl ether is added thereto at such a rate that the reaction temperature is kept below 5° C. After the completion of the addition, the reaction mixture is allowed to warm to room temperature and is stirred for 1 hour. To this white cloudy mixture is added a solution of 15.75 ml (0.10 mol) of 1-octanol and 16.7 ml (0.11 mol) of triethylamine in 50 ml of diethyl ether.

This mixture is then stirred for 16 hours at room temperature.

The white insoluble solids are filtered and the filtrate is concentrated under reduced pressure to give a yellow liquid. This liquid is treated with 200 ml of toluene and the resultant suspension is filtered. The filtrate is concentrated under reduced pressure to give 6.5 g (24%) of a colorless liquid: b.p. 92° C. (0.12 mm Hg).

EXAMPLE 2

2-Tert-butoxy-3-tert-butyl-1,3,2-oxazaphospholidine

A suspension of 3.7 g (0.033 mol) of potassium tert-butoxide and 0.3 ml of tetraglyme in 35 ml of toluene is admixed with a solution of 6.1 g (0.033 mol) of 3-tert-butyl-2-chloro-1,3,2-oxazaphospholidine in 35 ml of toluene. The rapidly stirred solution becomes cloudy immediately and is then heated at 100° C. for 16 hours. The white insoluble solids are filtered and the filtrate is concentrated under reduced pressure to give a colorless oil. This is then distilled under reduced pressure to give 1.9 (26%) of colorless liquid: b.p. 70° C. (0.2 mm Hg).

EXAMPLE 3

1,6-Bis(3-tert-butyl-1,3,2-oxazaphospholidin-2-yl-2-oxy)hexane

A rapidly stirred solution of 18.16 g (0.10 mol) of 3-tert.butyl-2-chloro-1,3,2-oxazaphospholidine in 110 ml of tetrahydrofuran (THF) is admixed with a solution of 13.6 ml (0.10 mol) of triethylamine and 5.91 g (0.05 mol) of 1,6-hexanediol in 110 ml of THF over a 15 minute period of room temperature. White precipitates are formed immediately and this is stirred at room temperature for 16 hours. The white insoluble solids are filtered and the filtrate is concentrated to give a clear liquid. This is distilled under reduced pressure to give 12.3 g (60.2%) of a clear liquid: b.p. 150° C. (0.05 mm Hg).

Anal. Calcd. for $C_{18}H_{38}N_2O_4P_2$: C, 52.9; H, 9.4; N, 6.9. Found: C, 52.4; H, 9.4; N, 6.8.

EXAMPLE 4

2-(2-Ethylhexyloxy)-3-tert-butyl-1,3,2-oxazaphospholidine

The procedure of Example 3 is repeated using 18.16 g (0.10 mol) of 3-tert-butyl-2-chloro-1,3,2-oxazaphospholidine in 115 ml of THF and 13.16 ml (0.10 mol) of triethylamine and 13.2 g (0.10 mol) of 2-ethylhexanol in 115 ml of THF to give 22.3 g (81.0%) of a clear liquid: b.p. 89°–92° C. (0.05 mm Hg).

Anal. Calcd. for C₁₄H₃₀NO₂P: C, 61.1; H, 11.0; N, 5.1. Found: C, 60.8; H, 11.1; N, 5.0.

EXAMPLE 5

2-(1-Adamantyloxy)-3-tert-butyl-1,3,2-oxazaphospholidine

A 500 ml, three neck flask equipped with a thermometer, an additional funnel and a condenser topped with a nitrogen sweep is charged with 2.62 g (0.06 mol) of sodium hydride. The sodium hydride is washed with two 20 ml portions of hexane and finally suspended in 30 ml of tetrahydrofuran. To the resultant suspension is added dropwise a solution of 9.12 g (0.06 mol) of 1-adamantanol in 75 ml of THF at such rate to keep the reaction temperature between 20°-30° C. The resulting yellow solution is warmed to approximately 40° C. for 1 hour and then cooled in an ice bath. A solution of 10.9 g (0.06 mol) of 3-tert-butyl-2-chloro-1,3,2-oxazaphospholidine in 75 ml of THF is added and stirring continued for 16 hours at room temperature. The resulting cloudy mixture is filtered and the solvent evaporated under reduced pressure. The residue is treated with 200 ml of toluene and the resultant suspension is filtered. The filtrate is concentrated in vacuo to yield a thick syrup. Triturating with methanol gives 6.0 g (33.6%) of a white solid: m.p. 48°-50° C.

Anal. Calcd. for C₁₆H₂₈NO₂P: C, 64.62; H, 9.49; N, 4.71. Found: C, 64.6; H, 9.7; N, 4.5.

EXAMPLE 6

2-(6,7,7-trimethyl-endo-[2,2,1]-bicycloheptyloxy)-3-tert-butyl-1,3,2-oxazaphospholidine The procedure of Example 5 is repeated using 2.4 g (0.05 mol) of sodium hydride with 25 ml of THF, 7.71 g (0.05 mol) of alpha-borneol (6,7,7-trimethyl-endo-[2.2.1]-bicycloheptanol) in 75 ml of THF and 9.1 g (0.05 mol) of 3-tert-butyl-2-chloro-1,3,2-oxaphospholidine in 75 ml of THF to give 10.0 g (66.8%) of a colorless oil.

Anal. Calcd. for C₁₆H₃₀NO₂P: C, 64.19; H, 10.10; N, 4.68. Found: C, 64.2; H, 10.5; N, 4.4.

EXAMPLE 7

This example illustrates the thermal stabilizing effectiveness of the instant stabilizers in combination with a phenolic antioxidant in polypropylene.

| Base | Formulation |
|---|---|
| Polypropylene* | 100 parts |
| Calcium Stearate | 0.10 parts |

*Profax 6501 from Hercules Chemical

Stabilizers are solvent blended into polypropylene as solutions in methylene chloride and after removal of the solvent by evaporation at reduced pressure, the resin is extruded using the following extruder conditions:

| | Temperature (°C.) |
|---|---|
| Cylinder #1 | 232 |
| Cylinder #2 | 246 |
| Cylinder #3 | 260 |
| Die #1 | 260 |
| Die #2 | 260 |
| Die #3 | 260 |
| RPM 100 | |

The melt flow rate (MFR) is determined by ASTM method 1238 condition L. The melt flow rate is a measure of the molecular weight for a specific type of polymer. The results are shown in Table I.

TABLE I

| | | MFR (g/10 min.) After Extrusion | |
|---|---|---|---|
| Additive | Conc. % | 1 | 5 |
| None | — | 4.8 | 8.9 |
| AO 1⁽¹⁾ | 0.1 | 2.7 | 4.3 |
| 0.1% AO 1⁽¹⁾ + Additive | | | |
| Example 3 | 0.05 | 2.3 | 2.4 |
| Example 4 | 0.05 | 2.2 | 2.1 |
| Example 6 | 0.05 | 1.9 | 2.3 |

⁽¹⁾AO 1 is neopentane tetrayl-tetrakis[3-(3',5'-di-tert-butyl-4'-hydroxyphenyl)propionate]

EXAMPLE 8

This example illustrates the color stabilizing effectiveness of the instant stabilizers in combination with a phenolic antioxidant in polypropylene. After each of the first, third and fifth extrusions, resin pellets from the extruder of Example 7 are compression molded into 125 mil (3.2 mm) thick plaques at 193° C. Specimen yellowness index (Y.I.) is determined according to ASTM D1925. The results are shown in Table II.

TABLE II

| | | YI Color After Extrusion | |
|---|---|---|---|
| Additive | Conc. % | 1 | 5 |
| None | — | 0.4 | 3.2 |
| AO 1⁽¹⁾ | 0.1 | 5.9 | 12.6 |
| 0.1% AO 1⁽¹⁾ + Additive | | | |
| Example 3 | 0.05 | −0.7 | 2.4 |
| Example 4 | 0.05 | 0.1 | 2.8 |
| Example 6 | 0.05 | 0.0 | 3.9 |

⁽¹⁾See Example 7

Summarizing, it is seen that this invention provides novel compounds which exhibit effective stabilization activity. Variations may be made in proportions, procedures and materials without departing from the scope of the invention as defined by the following claims.

What is claimed is:

1. A compound of the formula

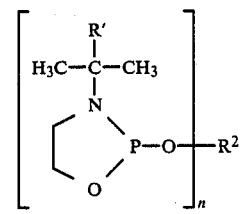

wherein
n is 1-4;
R' is alkyl of 1 to 5 carbon atoms, cycloalkyl of 5 to 6 carbon atoms, phenyl, phenyl substituted by alkyl of 1 to 18 carbon atoms, aralkyl of 7 to 9 carbon atoms or said aralkyl substituted by alkyl of 1 to 18 carbon atoms;
R², wherein n is 1, is alkyl of 1 to 18 carbon atoms, cycloalkyl of 5 to 12 carbon atoms, bicycloalkyl of 7 to 18 carbon atoms or tricyclic alkyl of 10 to 20 carbon atoms; and
R², when n is 2-4, is an n-valent aliphatic hydrocarbon of 1 to 18 carbon atoms.

2. The compound of claim 1, wherein n=1.

3. The compound of claim 2, wherein $R^2$ is $C_1-C_{18}$ alkyl.

4. The compound of claim 2, wherein $R^2$ is cycloalkyl of 5 to 12 carbon atoms, bicycloalkyl of 7 to 18 carbon atoms or tricyclic alkyl of 10 to 20 carbon atoms.

5. The compound of claim 1, wherein n=2-4.

6. The compound of claim 5, wherein n=2 and $R^2$ is $C_2-C_{10}$ alkylene, $C_2-C_{12}$ alkylidene, cyclohexylene, or polymethylene-propane-1,3-diyl.

7. The compound of claim 2, wherein R' is methyl and $R^2$ is $C_4-C_{12}$ alkyl.

8. The compound of claim 2, wherein R' is methyl and $R^2$ is cycloalkyl.

9. The compound of claim 6, wherein R' is methyl and $R^2$ is $C_4-C_{12}$ alkylidene.

10. 2-Octoxy-3-tert-butyl-1,3,2-oxazaphospholidine according to claim 3.

11. 2-Tert-butoxy-3-tert-butyl-1,3,2-oxazaphospholidine according to claim 3.

12. 1,6-Bis(3-tert-butyl-1,3,2-oxazaphospholidin-2-yl-2-oxy)hexane according to claim 6.

13. 2-(2-Ethylhexyloxy)-3-tert-butyl-1,3,2-oxazaphospholidine according to claim 3.

14. 2-(1-Adamantyloxy)-3-tert-butyl-1,3,2-oxazaphospholidine according to claim 4.

15. 2-(6,7,7-trimethyl-endo-[2,2,1]-bicycloheptyloxy)-3-tert-butyl-1,3,2-oxazaphospholidine according to claim 4.

16. A composition of matter comprising an organic material subject to oxidative, thermal and actinic degradation stabilized with an effective stabilizing amount of a compound of claim 1.

17. The composition of claim 16, wherein the organic material is a synthetic polymer.

18. The composition of claim 17, wherein the synthetic polymer is a polyolefin homopolymer or copolymer.

19. The composition of claim 18, which also contains a metal salt of a higher fatty acid.

20. The composition of claim 16 which also contains a phenolic antioxidant.

21. The composition of claim 19 which also contains a phenolic anitoxidant.

22. The composition of claim 20, wherein said phenolic antioxidant is selected from the group consisting of n-octadecyl 3,5-di-tert-butyl-4-hydroxyhydrocinnamate, neopentanetetrayltetrakis-(3,5-di-tert-butyl-4-hydroxylhydrocinnamate), di-n-octadecyl 3,5-di-tert-butyl-4-hydroxy-benzyl-phosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-di-oxacota-methylene bis(3-methyl-5-tert-butyl-4-hydroxyhydro-cinnamate), 2,6-di-tert-butyl-p-cresol, 2,2'-ethylidene-bis(4,6-di-tert-butylphenol), 1,3,5-tris(2,6-di-methyl-4-tert-butyl-3-hydroxybenzyl)isocyanurate, 1,1,3-tris-(2-methyl-4-hydroxy-5-tert-butylphenyl)butane, 1,3,5-tris-[2-(3,5-di-tert-butyl-4-hydroxyhydro-cinnamoyl-oxy)-ethyl]-isocyanurate, 3,5-di-(3,5-di-tert-butyl-4-hydroxybenzyl)-mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylenebis(3,5-di-tert-butyl-4-hydroxyhydrocinnamamide), calcium bis(ethyl-3,5-di-tert-butyl-4-hydroxybenzylphosphonate), ethylene bis[3,3-di(3-tert-butyl-4-hydroxyphenyl)butyrate], octyl, 3,5-di-tert-butyl-4-hydroxybenzylmercaptoacetate, bis(3,5-di-tert-butyl-4-hydroxyhydrocinnamoyl)hydrazide, and N,N'-bis[2-(3,5-tert-butyl-4-hydroxyhydroxo-cinnamoyloxy)ethyl]-oxamide.

23. The composition of claim 22, wherein said phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris-(3,5-di-tert-butyl-4-hydroxybenzyl)isocyanurate, 2,6-di-tert-butyl-p-cresol or 2,2'-ethylidene-bis(4,6-di-tert-butylphenol).

24. A method for stabilizing an organic material against oxidative, thermal and actinic degradation which comprises incorporating into said organic material an effective stabilizing amount of a compound of claim 1.

* * * * *